(12) United States Patent
Iwasaki et al.

(10) Patent No.: US 8,748,166 B2
(45) Date of Patent: Jun. 10, 2014

(54) SYSTEM FOR FORMING AND MAINTAINING BIOLOGICAL TISSUE

(75) Inventors: Kiyotaka Iwasaki, Tokyo (JP); Mitsuo Umezu, Tokyo (JP); Koji Kojima, Tokyo (JP); Charles Alfred Vacanti, Uxbridge, MA (US)

(73) Assignee: Waseda University, Tokyo (JP)

( * ) Notice: Subject to any disclaimer, the term of this patent is extended or adjusted under 35 U.S.C. 154(b) by 1050 days.

(21) Appl. No.: 12/681,049

(22) PCT Filed: Oct. 10, 2008

(86) PCT No.: PCT/JP2008/068450
§ 371 (c)(1),
(2), (4) Date: Jun. 22, 2010

(87) PCT Pub. No.: WO2009/051074
PCT Pub. Date: Apr. 23, 2009

(65) Prior Publication Data
US 2010/0261262 A1    Oct. 14, 2010

(30) Foreign Application Priority Data

Oct. 16, 2007  (JP) ................................ 2007-268448

(51) Int. Cl.
*C12M 3/00* (2006.01)
*A61F 2/04* (2013.01)

(52) U.S. Cl.
USPC .................. 435/293.1; 435/286.5; 435/284.1; 623/916

(58) Field of Classification Search
USPC ............. 435/284.1, 293.1; 623/916, 917, 921
See application file for complete search history.

(56) References Cited

U.S. PATENT DOCUMENTS

| | | | |
|---|---|---|---|
| 5,262,320 A * | 11/1993 | Stephanopoulos et al. ... | 435/403 |
| 5,792,603 A | 8/1998 | Dunkelman et al. | |
| 5,899,937 A * | 5/1999 | Goldstein et al. ............ | 623/2.11 |
| 6,921,662 B2 | 7/2005 | Takagi et al. | |
| 2004/0077072 A1 * | 4/2004 | Takagi et al. .............. | 435/284.1 |
| 2006/0212074 A1 * | 9/2006 | Umezu et al. ..................... | 607/1 |

FOREIGN PATENT DOCUMENTS

JP     9-313166 A    12/1997
JP     2003-284767 A    10/2003

(Continued)

OTHER PUBLICATIONS

International Search Report of PCT/JP2008/068450, mailing date of Jan. 13, 2009.

*Primary Examiner* — William H Beisner
(74) *Attorney, Agent, or Firm* — Westerman, Hattori, Daniels & Adrian, LLP

(57) ABSTRACT

A system (10) for forming and maintaining a biological tissue by which a biological tissue can be artificially formed by culturing cells, which comprises a pulse pump (12), a circulation pathway (13) having such a circuit structure as allowing a liquid cell culture medium discharged from the pulse pump (12) to return into the pulse pump (12), and a cell culture section (14A) and a gas exchange section (14B) provided along the circulation pathway (13). The cell culture section (14A) holds a cell holder (H) in such a manner to form a first channel wherein the liquid cell culture medium flowing in the circulation pathway (13) passes through the cell holder (H) and returns into the circulation pathway (13) and a second channel wherein the liquid cell culture medium flowing in the circulation pathway (13) passes outside the cell holder (H) and returns into the circulation pathway thereby bringing about a difference in pressure between the liquid cell culture medium passing through the respective channels.

4 Claims, 3 Drawing Sheets

(56) References Cited

FOREIGN PATENT DOCUMENTS

| JP | 2004-49185 A | 2/2004 |
|---|---|---|
| JP | 2006-105 A | 1/2006 |
| JP | 2006-109707 A | 4/2006 |
| WO | 97/49799 A1 | 12/1997 |
| WO | 02/90490 A1 | 11/2002 |

* cited by examiner

SYSTEM FOR FORMING AND MAINTAINING BIOLOGICAL TISSUE

TECHNICAL FIELD

The present invention relates to a system for forming and maintaining a biological tissue which system allows a biological tissue to be artificially formed by culturing cells forming the biological tissue and which also enables the functions of a biological tissue to be maintained ex vivo.

BACKGROUND ART

A blood vessel prosthesis has been proposed which is obtained by culturing smooth muscle cells using a porous scaffold material composed of a thermoplastic resin (see Patent Document 1). The blood vessel prosthesis is obtained by forming the scaffold material into a tube of thickness about 2 mm, filling the inside of the scaffold material with a collagen solution containing smooth muscle cells, and culturing the smooth muscle cells in the scaffold material in an incubator at 37° C. for about three days. In the blood vessel prosthesis, since the scaffold material is porous, the smooth muscle cells are distributed into the tube wall of the scaffold material without becoming necrotic.

Patent Document 1: Japanese Patent Publication No. 2003-284767

DISCLOSURE OF THE INVENTION

Problems to be Solved by the Invention

However, in the blood vessel prosthesis in the above-described Cited Document 1, the scaffold material remains as a core material. Thus, in the blood vessel prosthesis produced, endothelial cells, smooth muscle cells, and fibroblast are not constructed in layers in contrast to those in the human blood vessel.

Thus, given that cells forming a blood vessel are cultured in an incubator using, as a scaffold (base material), an in vivo degradable and absorptive polymer such as polyglycolic acid or poly($\epsilon$-caprolactone) which is soluble in vivo by hydrolysis, the resultant blood vessel prosthesis has a thickness of order of several $\mu$m. Thus, a vascular tissue with a millimeter-order thickness equivalent to the arterial blood vessel or the like is conventionally impossible to produce artificially.

Furthermore, there has been no system configured to maintain and store the functions of a tissue artificially formed as described above or a raw tissue for transplantation or the like ex vivo.

The present invention has been developed in view of these problems. An object of the present invention is to provide a system for forming and maintaining a biological tissue which system allows a biological tissue such as a vascular tissue to be artificially formed by culturing cells and also enables the functions of the biological tissue to be maintained ex vivo.

Means for Solving the Problems

To accomplish the above-described object, the present invention provides a system for forming and maintaining a biological tissue which system forms and maintains the biological tissue by immersing a cell holder in a liquid cell culture medium and culturing a cell of the biological tissue, the cell holder forming a space portion and consisting of a base with the cell attached thereto, the system comprising:

a pulse pump configured to apply a pulsatile flow to the liquid cell culture medium, a circulation pathway having a circuit configuration in which the liquid cell culture medium ejected from the pulse pump returns to the pulse pump, and a cell culture section and a gas exchange section both provided along the circulation pathway, wherein the circulation pathway comprises compliance means for carrying out amplitude adjustment on a pressure on the liquid cell culture medium, and resistance applying means located downstream of the compliance means to apply resistance to a flow of the liquid cell culture medium to adjust an average pulse pressure on the liquid cell culture medium, and the cell culture section holds the cell holder in such a manner as to form a first channel along which the liquid cell culture medium flowing through the circulation pathway passes through the space portion of the cell holder and returns into the circulation pathway and a second channel along which the liquid cell culture medium flowing through the circulation pathway passes outside the cell holder and returns into the circulation pathway, and the cell culture section causes a difference in pressure between the liquid cell culture medium flowing through the first channel and the liquid cell culture medium flowing through the second channel, and the gas exchange section supplies mixed gas containing oxygen and carbon dioxide to the liquid cell culture medium circulating through the circulation pathway to adjust a pH value of the liquid cell culture medium to a definite level.

Here, the cell culture section comprises a container main body with an internal space formed therein and a first open pathway, a second open pathway, a third open pathway, and a fourth open pathway which are open from the internal space toward outside, the first and second open pathways communicate with the space portion of the cell holder to form the first channel, and the third and fourth open pathways communicate with a portion of the internal space located outside the cell holder to form the second channel and is connected to a bypass pathway configured to bypass an area of the circulation pathway located downstream of the first channel, and the third and fourth open pathways thus utilize a change in pressure in the circulation pathway to cause a difference in pressure between the liquid cell culture medium flowing through the first channel and the liquid cell culture medium flowing through the second channel.

In the above-described configuration, the gas exchange section is preferably configured to enables even the liquid cell culture medium in the circulation pathway to be exchanged.

Advantages of the Invention

According to the present invention, when the cell forming the desired biological tissue to be formed is cultured, the pulsatile flow, which is similar to the human blood stream, can be applied to the liquid cell culture medium. Furthermore, the pH of the liquid cell culture medium can be set to a value similar to that of the blood through which the biological tissue passes. Furthermore, the cell culture section is configured to cause a difference in pressure between the liquid cell culture medium passing through the hollow portion corresponding to the inside of the cell holder and the liquid cell culture medium passing outside the cell holder. Thus, the cell culturing can be performed taking into account a difference in blood pressure between a vascular portion of the biological tissue through which blood actually flows and a portion thereof through which no blood flows. As a result, the cell is cultured in a self-renewal manner as in the case of the in vivo environment. Hence, the present inventors' experiments have demonstrated the possibility of forming a biological tissue of a thickness that cannot be conventionally achieved.

Furthermore, the system according to the present invention allows the in vivo blood stream condition to be reproduced. Thus, by allowing an artificially formed biological tissue or a raw biological tissue for transplantation to be held in the system, the functions of the biological tissue can be maintained ex vivo.

BEST MODE FOR CARRYING OUT THE INVENTION

An embodiment of the present invention will be described below with reference to the drawings.

Figure 1:
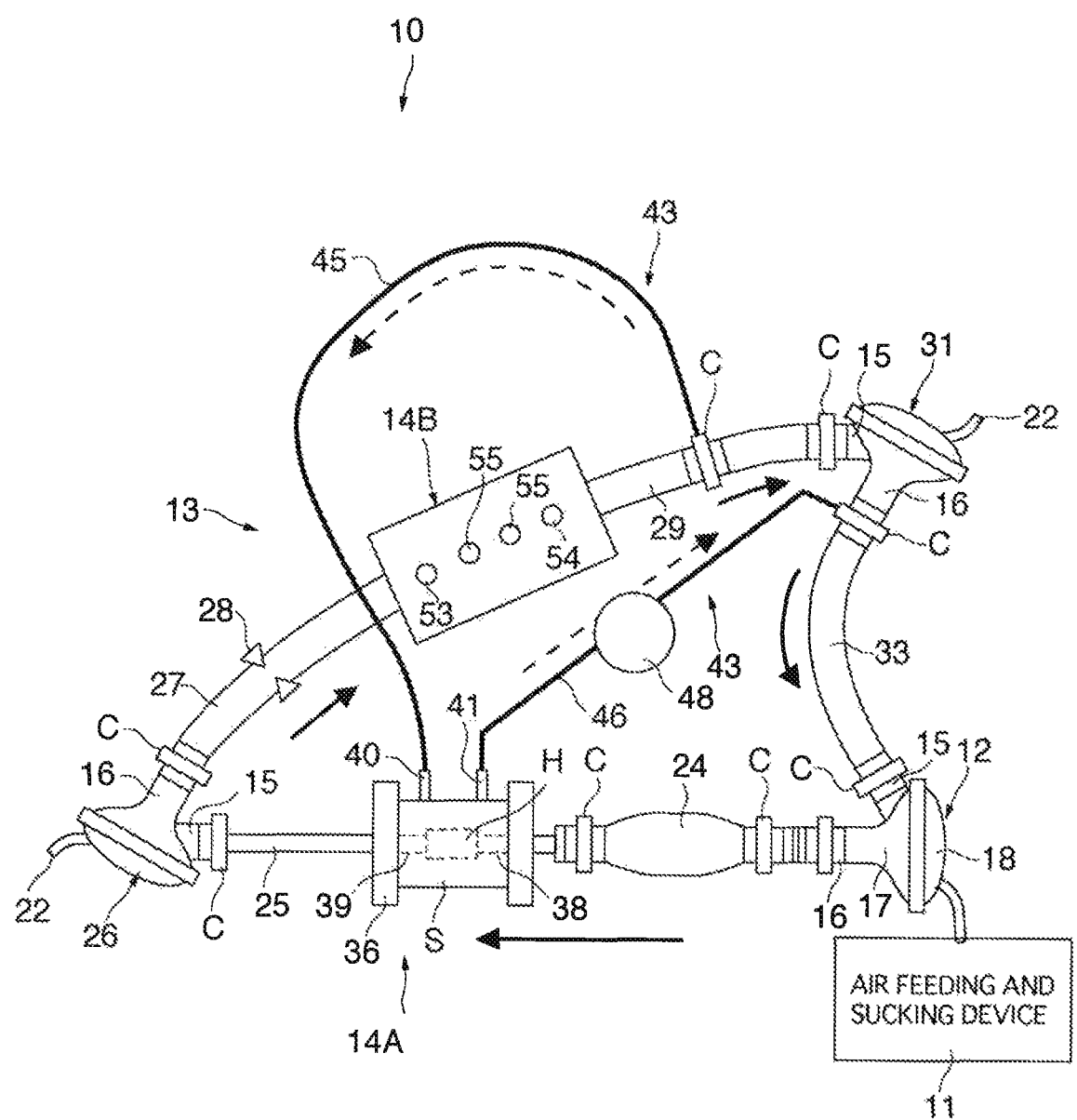
FIG. 1 is a schematic diagram showing the configuration of a system for forming and maintaining a biological tissue according to the present embodiment.

FIG. 1 shows a schematic diagram of the configuration of a system for forming and maintaining a biological tissue according to the present embodiment. In FIG. 1, the system 10 for forming and maintaining a biological tissue uses a liquid cell culture medium to culture cells forming a biological tissue, thus allowing a biological tissue to be self-formed. In the description below, the system 10 for forming and maintaining a biological tissue cultures various cells (smooth muscle cells, fibroblast, and endothelial cells) forming a blood vessel, to allow an arterial blood vessel inside the human body to be self-formed. Here, the liquid cell culture medium is a well-known solution enabling the various cells forming the blood vessel to be cultured.

The system 10 for forming and maintaining a biological tissue includes a well-known air feeding and sucking device 11, a pulse pump 12 made of polyurethane and connected to the air feeding and sucking device 11 to apply a pulsatile flow to the liquid cell culture medium, a circulation pathway 13 with a circuit structure in which the liquid cell culture medium ejected from the pulse pump 12 returns to the pulse pump 12, and a cell culture section 14A and a gas exchange section 14B both provided along the circulation pathway 13.

The air feeding and sucking device 11 has a well-known structure capable of feeding and sucking air to and from the pulse pump 12. The air feeding and sucking device 11 will not be described below in detail.

Figure 2:
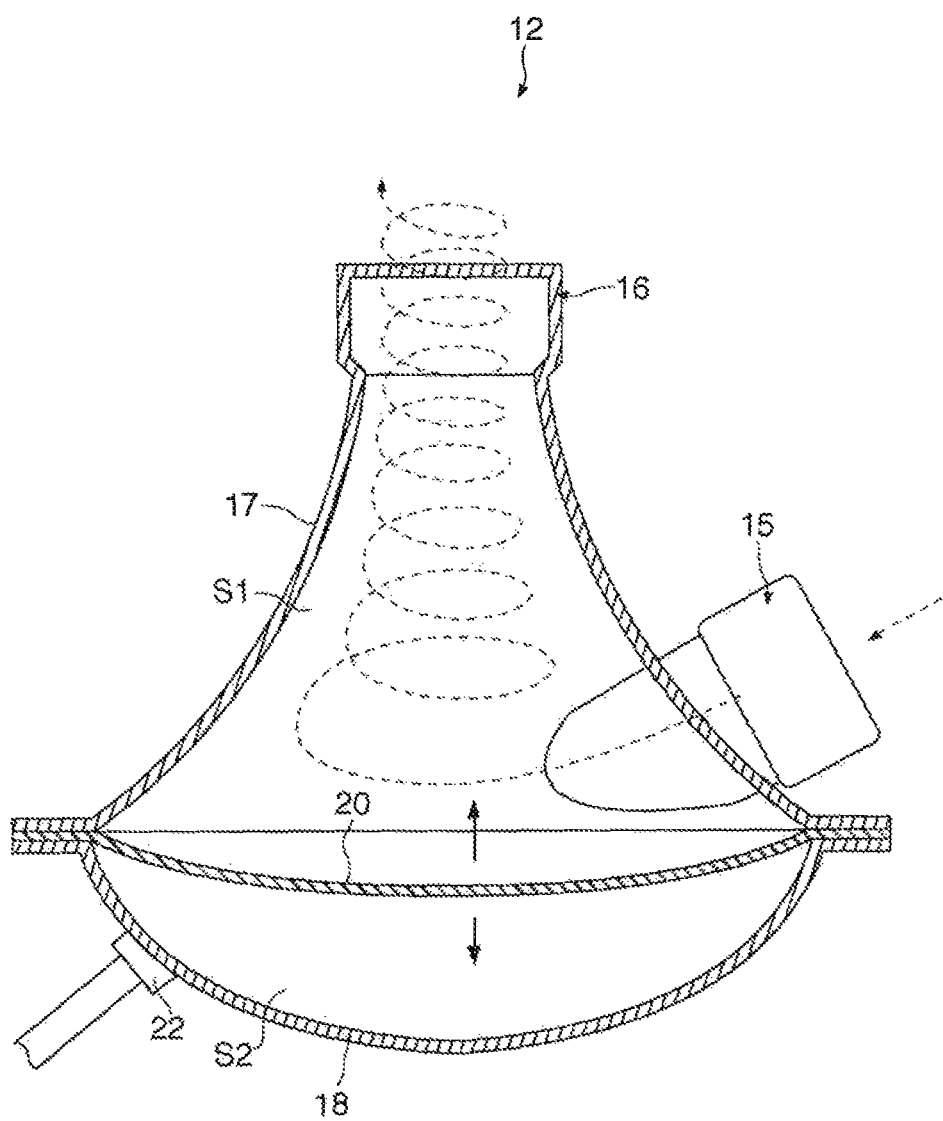
FIG. 2 is a schematic enlarged vertically sectional view of a pulse pump.

The pulse pump 12 is capable of internally generating a spiral vortex flow to generate a pulsatile flow during ejection. That is, as shown in FIG. 2, the pulse pump 12 includes a hollow upper structure 17 with a generally conical external shape and with an inflow port 15 and an outflow port 16 formed therein, a hollow lower structure 18 positioned under the upper structure 17 and having a generally domed external shape, and a flexible diaphragm 20 configured to partition internal spaces S1 and S2 in the structures 17 and 18 from each other. Here, the inflow port 15 is provided at the position of the right end, in FIG. 2, of the pulse pump 12 which end is connected to the peripheral wall of the upper structure 17. The outflow port 16 is provided at the upper end, in FIG. 2, of the pulse pump 12 which end corresponds to the top of the upper structure 17.

A vent hole 22 connected to the air feeding and sucking device 11 is provided in the lower structure 18 so as to allow compressed air to be alternately sucked from and fed into the lower internal space S2, at a definite timing. When compressed air is fed into and sucked from the internal space S2, the diaphragm 20 is displaced to increase and reduce the volume of the upper internal space S1. This causes a pulsatile flow to be generated in the liquid cell culture medium ejected from the outflow port 16. At this time, in the upper internal space S1, a spiral vortex flow that is unlikely to involve a flow interrupted area is generated as shown by a dashed line in FIG. 2. Although not particularly limited, in the present embodiment, the pressure (positive pressure) on air supplied to the inside of the internal space S2 is set to about 140 mmHg to 260 mmHg. On the other hand, the pressure (negative pressure) of air sucked from the internal space S2 is set to about −30 mmHg to −50 mmHg.

As shown in FIG. 1, the circulation pathway 13 has a channel configuration in which the liquid cell culture medium ejected by the pulse pump 12 is returned to the pulse pump 12 and can thus be circulated. That is, the circulation pathway 13 includes a compliance tube 24 connected between the outflow port 16 of the pulse pump 12 and the cell culture section 14A, a first connection tube 25 connected to the downstream side of the cell culture section 14A, a first connection pump 26 connected to the downstream side of the first connection tube 25, a second connection tube 27 connected between the first connection pump 26 and the gas exchange section 14B, resistance applying means 28 provided along the second connection tube 27 to apply flow resistance to the liquid cell culture medium, a third connection tube 29 connected to the downstream side of the gas exchange section 14B, a second connection pump 31 connected to the downstream side of the third connection tube 29, and a fourth connection tube 33 connected between the second connection pump 31 and the inflow port 15 of the pulse pump 12. Well-known connectors C are used to connect the above-described tubes and pumps 24 to 33 together.

The compliance tube 24 functions as compliance means for carrying out amplitude adjustment on the pulse pressure on the liquid cell culture medium ejected from the outflow port 16 of the pulse pump 12. The compliance tube 24 is formed of a gas-permeable resin material. Furthermore, the compliance tube 24 is formed of a soft material, for example, segmented polyurethane or silicon the thickness of which is varied to allow amplitude adjustment of the pulse pressure on the liquid cell culture medium to be supplied to the cell culture section 14A. In the present embodiment, the amplitude of the pulse pressure on the liquid cell culture medium to be supplied to the cell culture section 14A is set to, for example, ±20 mmHg of an average pulse pressure (100 mmHg) so as to approximate the amplitude of the adult pulse pressure. The average pulse pressure can be optionally adjusted to a value between the adult level and the infant level (40 mmHg).

The first to fourth connection tubes 25, 27, 29, and 33 are not particularly limited but is formed of vinyl chloride. Furthermore, a check valve (not shown in the drawings) is provided at each of the inlet and outlet of the pulse pump 12 so that the liquid cell culture medium can be reliably circulated in the direction of a solid arrow in FIG. 1 without flowing backward.

The first and second connection pumps 26 and 31 have the same configuration as that of the above-described pulse pump 12. Components of the first and second connection pumps 26 and 31 which are the same as or equivalent to the corresponding ones of the pulse pump 12 are denoted by the same reference numerals. Description of these components is thus omitted. The connection pumps 26 and 31 are also attached so as to be oriented such that the liquid cell culture medium flows into the pump through the inflow port 15 and flows out from the pump through the outflow port 16. Furthermore, the vent hole 22 in each of the connection pumps 26 and 31 is open to the outside so that the diaphragm 20 (see FIG. 2) is displaced in response to the flow of the liquid cell culture medium. Here, the amount of liquid cell culture medium filled in the circulation pathway 13 is slightly smaller than the maximum allowable amount of liquid cell culture medium filled in the circulation pathway 13. Thus, a damper effect is exerted such that displacement of the diaphragm 20 in each of the connection pumps 26 and 31 causes a pressure loss in the liquid cell culture medium. Thus, each of the connection pumps 26 and 31 functions as pressure attenuating means for gradually attenuating the fluid pressure on the liquid cell culture medium downstream. In the present embodiment, the fluid pressure on the liquid cell culture medium flowing through the second connection pump 31 to the fourth connection tube 33 is set to about 10 mmHg, which corresponds to the pressure in the human left atrium.

The resistance applying means 28 is provided at one point along the second connection tube 27 so as to act like the human peripheral resistance. Although not shown in detail, the resistance applying means 28 includes a pinch-like member configured to pinch the second connection tube 27. That is, since the resistance applying means 28 pinches the second connection tube 27, the minimum pressure on the liquid cell culture medium flowing upstream of the second connection tube 27 is prevented from reaching 0 mmHg in spite of pulsation of the pulse pump 12. This is a replication of the bloodstream in the human artery. Here, the average pulse pressure on the liquid cell culture medium flowing upstream of the second connection tube 27 can be adjusted to a definite value depending on how the second connection tube 27 is pinched. In the present embodiment, the average pulse pressure is adjusted to about 100 mmHg, substantially corresponding to the human average pressure. The resistance applying means 28 may be a member such as an variable aperture which exerts the above-described effects other than the above-described pinch-like member.

The cell culture section 14A includes a hollow container main body 36 with an internal spaces S formed therein, and a first open pathway 38, a second open pathway 39, a third open pathway 40, and a fourth open pathway 41 each of which is open from the internal space S toward the outside of the container main body 36.

The internal space S in the container main body 36 is closed off from the outside except for the open pathways 38 to 41. The internal space S is filled with the liquid cell culture medium. A hollow tube-like cell holder H configured to hold the above-described cells to be cultured is located so as to be immersed in the liquid cell culture medium. The cell holder H is formed by attaching cells to both the inside and outside of a tubular base material serving as a scaffold for the cells.

The first open pathway 38 is connected to the compliance tube 24. The second open pathway 39 is connected to the first connection tube 25. The cell holder H is connected to the first and second open pathways 38 and 39. In this connection state, the inside of the first and second open pathways 38 and 39 communicates with the hollow portion (space portion) of the cell holder H, that is, the inside thereof without external leakage. Hence, the pulsed liquid cell culture medium flowing from the compliance tube 24 into the first open pathway 38 passes through the cell holder H and flows out from the second open pathway 39 into the second connection tube 25. Thus, the first and second open pathways 38 and 39 form a first channel along which the liquid cell culture medium flowing through the circulation pathway 13 passes through the cell holder H and returns to the circulation pathway 13.

The third and fourth open pathways 40 and 41 connect to a bypass pathway 43 that allows definite areas of the third and fourth connection tubes 29 and 33 to be bypassed. The bypass pathway 43 consists of a first bypass tube 45 connected between the left one, in FIG. 1, of the third and fourth open pathways 40 and 41, that is, the third open pathway 40, and the middle portion of the third connection tube 29, and a second bypass tube 46 connected between the right one, in FIG. 1, of the third and fourth open pathways 40 and 41, that is, the fourth open pathway 41, and the middle portion of the fourth connection tube 33. A bypass pump 48 is provided along the second bypass tube 46. The bypass pump 48 is driven to allow the liquid cell culture medium to flow in the direction of a dashed arrow in FIG. 1. That is, part of the liquid cell culture medium flowing through the third connection tube 29 passes from the first bypass tube 45 and is thus fed to the internal space S in the container main body 36 through the third open pathway 40. The part of the liquid cell culture medium then flows from the fourth open pathway 41, through the second bypass tube 46, and out into the middle portion of the fourth connection tube 33. Thus, the third and fourth open pathways 40 and 41 form a second channel along which the liquid cell culture medium flowing through the circulation pathway 13 passes outside the cell holder H and returns into the circulation pathway 13. The connectors C are also used to connect the above-described tubes 29, 33, 45, and 46 together.

In this configuration, the liquid cell culture medium from the upstream compliance tube 24 on which a high pressure is exerted flows through the cell holder H. On the other hand, the liquid cell culture medium undergoing a lower pressure than the liquid cell culture medium flowing from the compliance tube 24 passes from the downstream third connection tube 29 to outside the cell holder H. That is, a difference in pressure occurs between the liquid cell culture medium flowing inside the cell holder H held in the cell culture section 14A and the liquid cell culture medium flowing outside the cell holder H.

Figure 3:
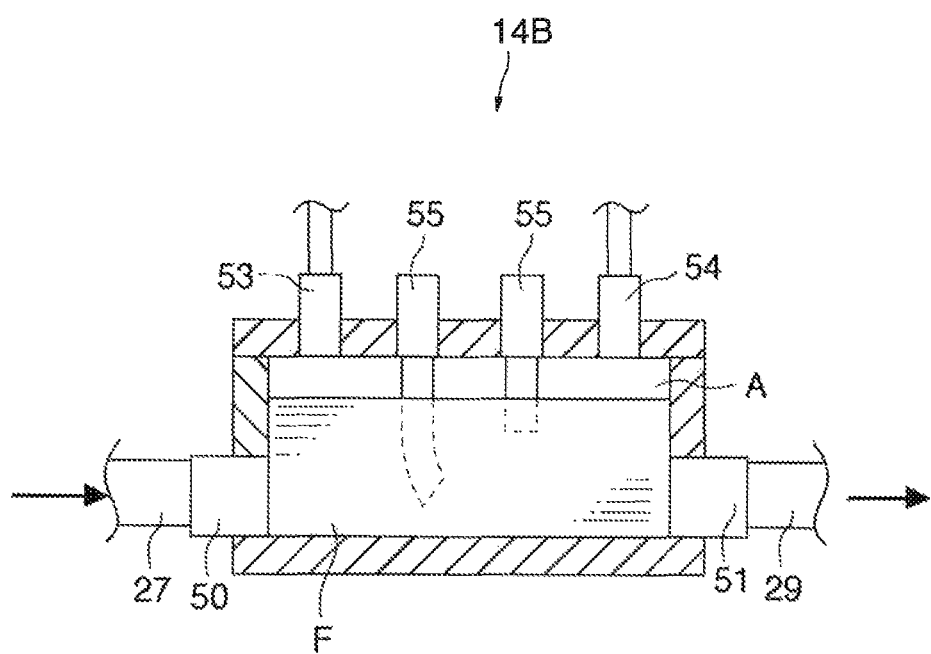
FIG. 3 is a schematic enlarged vertically sectional view of a gas exchange section.

As shown in FIG. 3, the gas exchange section 14B is formed like a box-shaped container with an accommodation space A in which the liquid cell culture medium F is accommodated. A fluid inflow port 50 and a fluid outflow port 51 are provided on the side surface of the gas exchange section 14B; the fluid inflow port 50 and the fluid outflow port 51 are in communication with the internal space A and are connected to the second and third connection tubes 27 and 29, respectively. The liquid cell culture medium F is carried into the accommodation space A in the gas exchange section 14B from the second connection tube 27 through the port 50 and flows out into the third connection tube 29 through the port 51. In the accommodation space A, the liquid cell culture medium F is accommodated with a gap maintained over the liquid cell culture medium F. Furthermore, an air supply port 53, an exhaust port 54, and fluid exchange ports 55, 55 are provided on the top surface of the gas exchange section 14B; the air supply port 53 allows external gas to be carried into the accommodation space A, the exhaust port 54 allows the gas to be discharged from the accommodation space A to the outside, and the fluid exchange ports 55, 55 allow the liquid cell culture medium F to flow into and out from the accommodation space A when the liquid cell culture medium F is exchanged.

A gas cylinder or the like (not shown in the drawings) is connected to the air supply port 53 so that mixed gas containing oxygen, carbon dioxide, and nitrogen and the concentration of which is controlled is fed from the gas cylinder into the accommodation space A in the gas exchange section 14B.

This allows the pH value (for example, 7.0 to 8.0) of the liquid cell culture medium F to be adjusted to a definite level. The pH value can be adjusted in accordance with the blood vessel or tissue to be produced. The fluid exchange port 55 is always closed except when the liquid cell culture medium F is exchanged so as to prevent air from flowing from the outside the gas exchange section 14B into the accommodation space A.

Now, the procedure of forming a blood vessel using the system 10 for forming and maintaining a biological tissue will be described in connection with the operation of the system 10 for forming and maintaining a biological tissue.

The cell holder H set in the cell culture section 14A includes a base material serving as a scaffold for the cells and rolled into multiple layers so as to form a tube wall, smooth muscle cells attached to the inner layer portion of the tube wall, fibroblast attached to the outer layer portion of the tube wall, and endothelial cells attached to the inner peripheral surface of the tube wall. The base material is a hydrolysable, in vivo degradable and absorptive polymer such as polyglycolic acid or poly(s-caprolactone).

With the cell holder H set in the cell culture section 14A, the inside of the circulation path 13 is filled with the liquid cell culture medium, and the pulse pump 12 is driven to actuate the system 10 for forming and maintaining a biological tissue. In this actuation condition, a pulsatile flow corresponding to the blood stream in the human aorta is applied to the liquid cell culture medium ejected from the pulse pump 12. The liquid cell culture medium then flows sequentially through the compliance tube 24, the first open pathway 38 in the cell culture section 14A, the inside of the cell holder H, and the second open pathway 39 and then out into the first connection tube 25. Subsequently, the liquid cell culture medium flows through the second to fourth connection tubes 27, 29, and 33 with the pressure on the liquid cell culture medium gradually reduced. Finally, the liquid cell culture medium flows similarly to the blood stream in the human vein before returning to the pulse pump 12. Here, the bypass pump 48 is simultaneously driven to allow part of the liquid cell culture medium flowing through the third connection tube 29 to flow through the bypass pathway 43. That is, part of the liquid cell culture medium flowing through the third connection tube 29 passes through the first bypass tube 45 into the internal space S located inside the cell culture section 14A and outside the cell holder H. Then, the part of the liquid cell culture medium flows through the second bypass tube 46 into the fourth connection tube 33. Here, the pressure on the liquid cell culture medium flowing through the bypass pathway 43 is not particularly limited but is adjusted to about 5 mmHg to about 10 mmHg in accordance with the degree of pinching by the resistance applying means 28 and the shapes, materials, and the like of the first and second bypass tubes 45 and 46. Thus, in the cell holder H with the vascular cells such as the smooth muscle cells, fibroblast, and endothelial cells attached thereto, the vascular cells are cultured while being exposed to the liquid cell culture medium with the flow condition thereof varying between the inside and outside the cell holder H. Specifically, inside the cell holder H, the liquid cell culture medium flows in a pulsatile flow condition similar to that of the human arterial flow. Outside the cell holder H, the liquid cell culture medium flows under a pressure close to the intrathoracic pressure outside the human blood vessels. Furthermore, the gas exchange section 14B is supplied with, for example, mixed gas containing about 5% of carbon dioxide and about 0.1% of oxygen, at a definite timing. Thus, during the circulation process, the pH of the liquid cell culture medium is kept at 7.3 to 7.5, which corresponds to the pH of the blood in the artery. Hence, the vascular cells can be cultured using the liquid cell culture medium in almost the same condition as that of the arterial blood vessel present in the human body. Thus, a condition almost like in vivo renewal of the tissue can be successfully produced.

The present inventors carried out the following experiments. Under the above-described conditions, the system 10 for forming and maintaining a biological tissue was operated for about two weeks. During this period, the flow rate of the liquid cell culture medium was gradually increased up to 0.5 l/min, corresponding to the adult blood flow rate, with the liquid cell culture medium appropriately exchanged for new one. With the base material hydrolyzed, the vascular cells were formed into a blood vessel-like tissue of length 5 cm, inner diameter 6 mm, and thickness 2 mm. The inner diameter and thickness of the blood vessel-like tissue thus obtained were equivalent to those of the arterial blood vessel. Thus, the conventionally impossible, pure arterial blood vessel containing almost no artifact was successfully artificially formed.

Therefore, such an embodiment enabled a conventionally impossible blood vessel-like tissue with a thickness of millimeter order to be created by cell culturing.

In the above-described embodiment, the present invention is applied as a system for allowing an arterial blood vessel to be self-formed by culturing cells forming a blood vessel. However, the system according to the present invention is not limited to such an application. That is, if for example, a venous vessel is self-formed, the cell culture section 14A may be located in a portion of the circulation pathway 13 which corresponds to the blood stream condition in the venous vessel, that is, along the third connection tube 29, so that the flow condition of the liquid cell culture medium flowing through the cell holder H can be set the same as the actual blood stream condition. Then, the components of mixed gas injected into the gas exchange section 14B may be adjusted to set the pH value of the liquid cell culture medium equal to that of the blood flowing through the actual vein. Alternatively, the present system can be used to produce not only blood vessels but also biological tissues in other organs or the like. In this case, a biological tissue is expected to be artificially produced as follows. Cells of the desired biological tissue are attached to a base material to form the hollow cell holder H, the base material including a space portion shaped like a tube, a bag, or a valve and through which the liquid cell culture medium can pass. Then, the pH and flow condition of the liquid cell culture medium inside and outside the cell holder H is appropriately adjusted based on the condition of the blood flow in the blood vessel through which the biological tissue passes as well as the surrounding conditions.

Furthermore, in the above-described embodiment, the gas exchange section 14B is located between the second and third connection tubes 27 and 29. However, the gas exchange section 14B may be located at any position along the circulation pathway 13 as long as the pH of the liquid cell culture medium can be adjusted.

Moreover, the cell holder H may initially be weakly connected to the first and second open pathways 38 and 39 to allow the liquid cell culture medium to leak from the inside of the cell holder H through the connection between the cell holder H and each of the first and second open pathways 38 and 39. A given time later, the connections may be made firmer so that the leakage does not occur anymore. This allows the liquid cell culture medium to spread even to the connection between the cell holder H and each of the first and second open pathways 38 and 39. Thus, the cell culturing condition on the cell holder H can be made more uniform.

Furthermore, when an artificially formed biological tissue or a raw biological tissue for transplantation or the like is held on the cell holder H and the system 10 for forming a biological tissue is operated using a liquid cell culture medium, artificial blood, or the like as described above, the biological tissue can be stored with the functions thereof maintained ex vivo.

Additionally, the configurations of the components of the system according to the present invention are not limited to the illustrated configuration examples but may be varied as long as the components operate in substantially the same manner.

INDUSTRIAL APPLICABILITY

The system according to the present invention enables a biological tissue configured similarly to the actual tissue in the living body to be artificially formed by cell culturing, thus allowing a very biologically compatible, artificial biological tissue to be manufactured. The system according to the present invention can also be utilized as a maintenance system for allowing the biological tissue to be stored with the functions thereof maintained ex vivo. Alternatively, the system according to the present invention can be utilized as a system for differentiating and inducing cells inherent in an organ from stem cells or any of various evaluation systems for biological tissues.

The invention claimed is:

1. A system for forming and maintaining a biological tissue which system forms and maintains the biological tissue by immersing a cell holder in a liquid cell culture medium and culturing a cell of the biological tissue, the cell holder forming a space portion and having a base with the cell attached thereto, the system comprising:
   a pulse pump configured to apply a pulsatile flow to the liquid cell culture medium, a circulation pathway having a circuit configuration in which the liquid cell culture medium ejected from the pulse pump returns to the pulse pump, and a cell culture container and a gas exchanger both provided along the circulation pathway,
   wherein the circulation pathway includes a compliance amplitude adjustor configured to adjust amplitude on a pressure on the liquid cell culture medium, and a resistance applier located downstream of the compliance amplitude adjustor configured to apply resistance to a flow of the liquid cell culture medium to adjust an average pulse pressure on the liquid cell culture medium, and the cell culture container is configured to hold the cell holder such as to form a first channel along which the liquid cell culture medium flowing through the circulation pathway passes through a space portion of the cell holder and returns into the circulation pathway and a second channel along which the liquid cell culture medium flowing through the circulation pathway passes outside the cell holder and returns into the circulation pathway, and the cell culture container is configured to maintain a difference in pressure between the liquid cell culture medium flowing through the first channel and the liquid cell culture medium flowing through the second channel,
   the gas exchanger is configured to supply mixed gas containing oxygen and carbon dioxide to the liquid cell culture medium circulating through the circulation pathway to adjust a pH value of the liquid cell culture medium to a definite level,
   wherein the cell culture container comprises a container main body with an internal space formed therein and a first open pathway, a second open pathway, a third open pathway, and a fourth open pathway which are open from the internal space toward outside,
   the first and second open pathways communicate with the space portion of the cell holder to form the first channel, and
   the third and fourth open pathways communicate with a portion of the internal space located outside the cell holder to form the second channel that is connected to a bypass pathway configured to bypass an area of the circulation pathway located downstream of the resistance applier such that the third and fourth open pathways utilize a change in pressure in the circulation pathway to maintain a difference in pressure between the liquid cell culture medium flowing through the first channel and the liquid cell culture medium flowing through the second channel.

2. The system for forming and maintaining a biological tissue according to claim 1, wherein the gas exchanger is configured to enable the liquid cell culture medium in the circulation pathway to be exchanged.

3. The system for forming and maintaining a biological tissue according to claim 1, wherein said compliance amplitude adjustor includes a soft compliance tube.

4. The system for forming and maintaining a biological tissue according to claim 3, wherein said resistance applier includes a pincher or a variable aperture.

* * * * *